United States Patent
McCook et al.

(10) Patent No.: US 8,182,793 B2
(45) Date of Patent: *May 22, 2012

(54) SUNLESS TANNING PRODUCTS AND PROCESSES

(75) Inventors: John Patrick McCook, Frisco, TX (US); Philip J. Gordon, Plano, TX (US); D. Craig Woodward, Plano, TX (US)

(73) Assignee: Concept Laboratories

( * ) Notice: Subject to any disclaimer, the term of this patent is extended or adjusted under 35 U.S.C. 154(b) by 1037 days.

This patent is subject to a terminal disclaimer.

(21) Appl. No.: 11/015,569

(22) Filed: Dec. 18, 2004

(65) Prior Publication Data

US 2006/0134027 A1 Jun. 22, 2006

(51) Int. Cl.
*A61K 8/00* (2006.01)
*A61K 8/18* (2006.01)
*A61K 31/74* (2006.01)
*A61K 31/12* (2006.01)
*A61K 31/045* (2006.01)
*A61Q 17/04* (2006.01)
*A01N 35/00* (2006.01)
*A01N 31/00* (2006.01)

(52) U.S. Cl. ....... 424/59; 424/78.03; 514/675; 514/724; 514/738

(58) Field of Classification Search ............... 424/59, 424/60, 400, 401, 78.03; 514/675, 724, 738
See application file for complete search history.

(56) References Cited

U.S. PATENT DOCUMENTS

| | | | | |
|---|---|---|---|---|
| 5,318,774 A | * | 6/1994 | Alban et al. | 424/59 |
| 5,700,452 A | * | 12/1997 | Deckner et al. | 424/59 |
| 6,113,888 A | * | 9/2000 | Castro et al. | 424/59 |
| 6,231,837 B1 | * | 5/2001 | Stroud et al. | 424/59 |
| 7,014,842 B2 | * | 3/2006 | Dueva-Koganov et al. | 424/59 |
| 2003/0180335 A1 | * | 9/2003 | Ohmori et al. | 424/401 |

OTHER PUBLICATIONS

Nonstatutory Obviousness-type Double Patenting as being unpatentable over claims 1-6 of co-pending U.S. Appl. No. 11/394,940.*

* cited by examiner

*Primary Examiner* — Johann Richter
*Assistant Examiner* — Mei-Ping Chui
(74) *Attorney, Agent, or Firm* — Louis C. Paul

(57) ABSTRACT

Aqueous sunless tanning formulations employed for automatic spray systems with enhanced tanning and skin moisturization properties.

5 Claims, No Drawings

SUNLESS TANNING PRODUCTS AND PROCESSES

CROSS REFERENCE TO CO-PENDING APPLICATIONS

The present application is related to two co-pending applications of John McCook et al, Ser. No. 10/382,868 titled SUNLESS TANNING PRODUCTS AND PROCESSES, filed on Mar. 5, 2003 and a similar application of like title, Ser. No. 10/694,972, filed Oct. 28, 2003. Both of these applications and the present application have a common sole assignee.

FIELD OF THE INVENTION

The present invention describes novel sunless tanning compositions having properties that result in enhanced tanning characteristics.

BACKGROUND OF THE INVENTION

Sunless tanning, also called self-tanning, is the ability to impart a tan to fair or light skin without the use of sunlight. In order to achieve a tanned look or otherwise darken their skin, individuals can expose their skin to sunlight or a source of simulated sunlight, e.g., a solar simulator or ultraviolet lamps. For many individuals, such exposure will stimulate formation of new melanin pigment and the retention of increased amount of melanin in the epidermis and produce a darkened skin color. However, some individuals find that such exposure does not produce the desired melanin formation and as a result the desired tan is not obtained. It is also well known that, as light skin humans age, the ability to produce melanin through ultraviolet light stimulation diminishes significantly. Exposure to the sun or a source of ultraviolet radiation can have deleterious effects for many individuals and can, in fact, cause sunburn, skin blistering, premature skin aging or skin cancer. Self-tanning or sunless tanning compositions offer a safe alternative and enable these individuals to obtain the desired tanned look.

Commercial formulations, using dihydroxyacetone [DHA], or DHA in combination with other reducing sugars such as 1,3,4-trihydroxy-2-butanone (erythrulose), applied locally to the skin, were developed for this purpose. Typical sunless tanning preparations sold to the consumer are in the form of a cream, lotion, gel or aerosol foam or spray. Additionally, within the last few years, indoor tanning salons have begun to offer automated sunless tanning spray applications as a safe alternative to UV tanning beds. These sunless tanning sprays are applied either in an enclosed booth or with a hand-held spray apparatus and involve the pressurized application of a sunless tanning solution containing DHA or combinations of DHA and erythrulose and are typically delivered over the entire body in the form of a mist.

Sunless tanning booth operations and automated spray systems for coating human skin with various cosmetic compositions including self-tanning compositions are known to the art.

The sunless tanning solutions used in these automated sunless tanning spray systems utilize relatively high levels of DHA (7-12%) versus the typical packaged sunless tanning creams, lotions, foams and sprays (3-7% DHA) sold in various retail outlets. Moreover, the automated sunless tanning spray systems deliver a mist of several ounces of sunless tanning solution in one misting session; much more sunless tanning product than typically would be self-applied by a consumer of a packaged sunless tanning product in any single application.

Sunless tanning booth sprays can coat the entire body with a light mist in one minute or less. Hand-held automated sunless tanning sprays utilizing an airbrush technique require several minutes to cover large areas of exposed skin. These pressurized spray systems dry quickly and produce a natural-looking tan. The spray booth systems, in particular, avoid the need for a second person to apply a sunless tanning cream, lotion, or foam product to hard to reach areas of the body. The sunless tanning booth sprays and hand-held pressurized sprays are "simple" aqueous solutions of DHA without the need for oils, emulsifiers, surfactants, polymers, and other stabilizers that can result in greasiness, stickiness, and longer drying times. This fast drying characteristic of these sunless tanning automated misting systems can be an advantage over conventional sunless tanning creams, lotions, gels, and foams.

Complete drying of the sunless tanning formulation is necessary to avoid staining of clothing. Conventional sunless tanning products caution the consumer to wait 15 minutes or more until the sunless tanning product applied is completely dry before dressing or contact with clothing. Sunless tanning solutions applied via automated misting systems are dry within one-two minutes after application. Automated sunless tanning formulations contain water soluble ingredients, are oil-free and exhibit low viscosity (e.g, less than 200 cps). These characteristics are required not only to speed drying but to avoid clogging of the spray nozzles and to facilitate the misting process without excessive back pressure.

The malodor issues associated with the automated tanning sprays has been solved with the use of 1,2-pentylene glycol as described in the two co-pending applications of John McCook et al; Ser. No. 10/382,868 and Ser. No. 10/694,972, titled SUNLESS TANNING PRODUCTS AND PROCESSES. Commercial application of this sunless tanning technology has resulted in improved results—darker, more even and low odor or odorless formulations vs. conventional technology. However, a small number of users of the new sunless tanning formulation, estimated at less than 1%, have experienced occasional skin dryness during the winter season in North America. This skin dryness is characterized by an uneven, dry, or mottled appearance on certain areas of the arms or legs of users within 24 hours of product application. Although the improved self-tanning formulations described in co-pending application Ser. No. 10/694,972 contain 1,2-pentylene glycol and other glycols that have humectant or moisturizing properties, the moisturizing properties are insufficient for a small number of consumers prone to dry or very dry skin, manifested particularly in the winter months. A novel approach for solving this skin dryness issue has been discovered through the addition of lactate salts.

SUMMARY OF THE INVENTION

A search for additives that would effectively eliminate any skin dryness issues associated with the use of automated self tanning spray formulations containing 1,2-pentylene glycol and other diols began with an evaluation of water soluble cosmetic or pharmaceutical additives that would be compatible with DHA based sunless tanning formulations and show sustained hydration of the skin (water binding properties) and have the ability to reduce water activity ($a_w$), in vivo.

Water activity of sunless tanning formulations can be an important consideration for maximizing the tanning response of Dihydroxyacetone (DHA). Although water activity measurements are rarely used by the Cosmetic Industry, measurements of water activity of food materials and processed food products are very important in the development and processing and packaging of food to maintain adequate shelf life, optimize flavor, and avoid microbial spoilage. A comprehensive review of water structure and behavior, including a description of water activity is given by Martin Chaplin (http://www.martin.chaplin.btinternet.co.uk/index.html).

The description of water activity is abstracted from the references given at this web site. When water interacts with solutes and surfaces, it is unavailable for other hydration interactions. The term 'water activity' ($a_w$) describes the (equilibrium) amount of water available for hydration of materials; a value of unity indicates pure water whereas zero indicates the total absence of water molecules. As described above, it has particular relevance in food chemistry and preservation. Water activity is the effective mole fraction of water, defined as $a_w = I_w x_w = p/p_0^a$ where $I_w$ is the activity coefficient of water, $x_w$ is the mole fraction of water in the aqueous fraction, p is the partial pressure of water above the material and $p_0$ is the partial pressure of pure water at the same temperature (i.e. the water activity is equal to the equilibrium relative humidity (ERH), expressed as a fraction). It may be experimentally determined from the dew-point temperature of the atmosphere in equilibrium with the material. A high $a_w$ (i.e. >0.8) indicates a 'moist' or 'wet' system and a low $a_w$ (i.e. <0.7) generally indicates a 'dry' system. Water activity reflects a combination of water-solute and water-surface interactions plus capillary forces.

It is also well known from published literature that water activity can change reaction rates. Generally, chemical reactions proceed faster at higher water activity indices (e.g. <0.4) and peak at 0.8. However certain chemical reactions, notably the Maillard reaction, have a non-linear relationship with water activity indices.

The Maillard reaction is responsible for the non-enzymatic browning of foods (e.g., baked cookies) and involves the reaction of simple sugars (carbonyl groups) and amino acids (free amino groups). They begin to occur at lower temperatures and at higher dilutions than caramelization and increase with temperature and time and this reaction is impacted by water activity as indicated by published studies of Eichner and Karel beginning with a publication in 1972 (Eichner, K and Karel, M.; *J. Agric. Food Chem.* (1972) 20:218)

EXHIBIT 1

The Maillard Reaction (Initial Reaction)

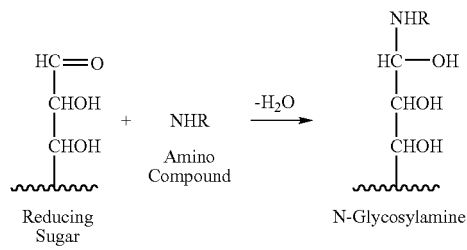

Maillard reactions have three basic phases. The initial reaction is the condensation of the carbonyl group of a reducing sugar (e.g., aldose) with a free amino group of a protein or an amino acid, which loses a molecule of water to form N-substituted glycosylamine. This is unstable and undergoes the "Amadori rearrangement" to form "1-amino-1-deoxy-2-ketoses" (known as "ketosamines"). The ketosamine products of the Amadori rearrangement can then react three ways in the second phase. One is simply further dehydration (loss of two water molecules) into reductones & dehydro reductones. These are essentially "caramel" products and in their reduced state are powerful antioxidants. A second is the production of short chain hydrolytic fission products such as diacetyl, acetol, pyruvaldehyde, etc. These then undergo "Strecker degradation" with amino acids to aldehydes and by condensation to aldols, or they may react in the absence of amino compounds, to give aldols and high molecular weight, nitrogen-free polymers. A third path is the Schiff's base/furfural path. This involves the loss of 3 water molecules, then a reaction with amino acids and water. All these products react further with amino acids in the third phase to form the brown nitrogenous polymers and copolymers called melanoidins.

Water is produced during the Maillard reaction. Thus, as a consequence of the law of mass action, the reaction occurs less readily in foods with a high $a_w$ value. In addition, the reactants are diluted at high $a_w$ values while, at low $a_w$, the mobility of reactants is limited, despite their presence at increased concentration. In practice, the Maillard reaction occurs most rapidly at intermediate $a_w$ values (0.5-0.8), and $a_w$ is of most significance to the reaction in dried and intermediate-moisture foods (IMFs), which have $a_w$ values in this range.

The background information concerning the Maillard reaction and water activity is of particular importance for sunless tanning formulation and processes and the development of improved sunless tanning compositions. Although it is well known that the Maillard reaction is responsible for the development of a sunless tan on a person by way of the reaction of dihydroxyacetone, a reducing sugar, with the amino acids present in the keratin of the top layers of the skin, the influence of water activity on the performance of sunless tanning formulations has not been reported in published literature.

Given the influence of water activity on the Maillard reaction in terms of increased speed of reaction at moderate levels of water activity ($a_w$=0.5-0.8), measurement of water activity of sunless tanning formulations and formula additives and the effect of these additives on the water activity of the tanning reaction in vivo and the affect on product performance (speed of tanning, color intensity, quality of color, tan longevity, evenness of color, skin moisturization, product stability, product odor, etc.) is an important consideration that, heretofore, has been overlooked.

Water activity describes the continuum of energy states of the water in a system. The water in a sample appears to be "bound" by forces to varying degrees. This is a continuum of energy states, rather than a static "boundness." Water activity is sometimes defined as the amount of "bound" vs. "free" or "available water" in a system. These terms are easier to conceptualize, although they fail to adequately define all aspects of the concept of water activity. Water activity instruments measure the amount of free (sometimes referred to as unbound or active) water present in the sample. A portion of the total water content present in a product is strongly bound to specific sites on the chemicals that comprise the product. These sites may include the hydroxyl groups of polysaccharides, the carbonyl and amino groups of proteins, and other polar sites. Water is held by hydrogen bonds, ion-dipole bonds, and other strong chemical bonds. Some water is bound less tightly, but is still not available (e.g., as a solvent for water-soluble food components). Many preservation processes attempt to eliminate spoilage by lowering the availability of water to microorganisms. Reducing the amount of free—or unbound—water also minimizes other undesirable chemical changes that occur during storage. The processes used to reduce the amount of free water in consumer products include techniques like concentration, dehydration and freeze drying. Freezing is another common approach to controlling spoilage. Water in frozen foods is in the form of ice crystals and therefore unavailable to microorganisms for reactions with food components. Because water is present in varying degrees of free and bound states, analytical methods that attempt to measure total moisture in a sample may produce different results. Therefore, water activity tells the real story.

There is no device that can be put into a product to directly measure the water activity. However, the water activity of a product can be determined, indirectly, from the relative humidity of the air surrounding the sample when the air and the sample are at equilibrium. Therefore, the sample must be in an enclosed space where this equilibrium can take place. Once this occurs, the water activity of the sample and the relative humidity of the air are equal. The measurement taken at equilibrium is called an equilibrium relative humidity or ERH.

In practice, water activity can be determined by use of the Aqualab© (Decagon, Inc., Pullman, Wash.) or HygroLab© (Rotronic, Inc., Huntington, N.Y.). For all of the experimental water activity data recorded and detailed in this application, an Aqualab 3T-E instrument with an accuracy of +/−0.003 units and with automatic temperature equilibration (23.7+/− 0.2° C.) capability was utilized.

In the AquaLab instrument, a sample is equilibrated within the headspace of a sealed chamber containing a mirror, an optical sensor, an internal fan, and an infrared temperature sensor. At equilibrium, the relative humidity of the air in the chamber is the same as the water activity of the sample. A thermoelectric (Peltier) cooler precisely controls the mirror temperature. An optical reflectance sensor detects the exact point at which condensation first appears. A beam of infrared light is directed onto the mirror and reflected back to a photodetector which detects the change in reflectance when condensation occurs on the mirror. A thermocouple attached to the mirror accurately measures the dew-point temperature. The internal fan is for air circulation, which reduces vapor equilibrium time and controls the boundary layer conductance of the mirror surface. Additionally, a thermopile sensor (infrared thermometer) measures the sample surface temperature. Both the dew point and sample temperatures are then used to determine the water activity. During a water activity measurement, the AquaLab repeatedly determines the dew-point temperature until vapor equilibrium is reached. Since the measurement is based on temperature determination, calibration is not necessary, but measuring a standard salt solution checks proper functioning of the instrument. If there is a problem, the mirror is easily accessible and can be cleaned in a few minutes.

Sunless tanning formulations typically contain 3-10% by weight of DHA as the primary tanning agent dissolved in water. DHA is a water soluble sugar, and, as with other sugars or solutes will decrease the water activity as compared to pure water ($a_w$=1.00). Solutes dilute the water, increasing its entropy and therefore lowering its energy state. These two effects combine to lower the total free energy of the water. Water activity of commercial sunless tanning products were found to be typically in a range of 0.950-0.985. The DHA together with glycerin, glycols, or other humectants are most likely responsible for the vast majority of the reduction in $a_w$ of sunless tanning formulations based on the $a_w$ data for simple solutions of DHA and humectants measured by the Aqualab 3TE and shown in Table 1 below:

TABLE 1

| 5% DHA solutions (w/w) | | 10% DHA solutions (w/w) | |
|---|---|---|---|
| Solution mixture | Water activity ($a_w$) | Solution mixture | Water activity ($a_w$) |
| +95% Deionized Water | 0.993 | +10% Deionized Water | 0.985 |
| +5% pentylene glycol +90% Deionized Water | 0.987 | +5% pentylene glycol +85% Deionized Water | 0.977 |
| +10% pentylene glycol +85% Deionized Water | 0.980 | +10% pentylene glycol +80% Deionized Water | 0.971 |
| | | +5% pentylene glycol +5% butylene glycol +80% Deionized Water | 0.968 |
| | | +5% ethoxydiglycol +5% butylenes glycol +80% Deionized Water | 0.970 |
| | | +5% isoprene glycol +5% butylenes glycol +80% Deionized Water | 0.968 |
| | | +10% glycerol +80% Deionized Water | 0.961 |

Interestingly, glycerol, commonly used in sunless tanning formulations for humectancy or skin moisturization appears to lower the water activity to a greater extent than the other glycols evaluated. However, earlier studies conducted by the applicant and detailed in prior filings for sunless tanning processes (Ser. No. 10/382,868 & Ser. No. 10/694,972) show that glycerol has somewhat of an inhibitory effect on the tanning response of DHA.

A general review of the literature for the use of cosmetic or pharmaceutical raw materials for reduction of water activity did not disclose any specific ingredients or additives that were specifically used based upon the potential for reducing $a_w$. However, a wide range of cosmetic and pharmaceutical additives are identified in the published literature as "humectants", "moisturizers", "water scavengers", water absorbents", "water retention aids", or as "water-loss regulators". The Cosmetic & Personal Care Additives Electronic Handbook; 2002, produced by Synapse Information Resources, Inc. of Endicott, N.Y. lists thousands of cosmetic additives including ingredients in the aforementioned categories.

For an ingredient to reduce water activity, it must be soluble in water. This criterion alone eliminates a vast number of cosmetic ingredients that are otherwise characterized as humectants or moisturizers or water retention aids. For example, cellulosic and starch graft polymers such as carboxy methylcellulose, carboxymethyl hydroxyethylcellulose, sodium carboxymethylcellulose, and starch/acrylates/acrylamide copolymers have water absorbent and water retention properties attributed to them. These polymers absorb water and can create water-polymer gels at low concentrations, but they do not significantly alter water activity at use concentrations. Other humectants that contain a reactive amino nitrogen or exist only at an alkaline pH are not compatible with DHA. Most other water soluble humectants, stable within an acidic pH range, e.g., pH 3.0-6.0, generally fall into one of the three categories of water soluble sugars & polyols, dihydroxyl or diglycol compounds, and certain salts. The polyols and dihydroxyl compounds are covered quite comprehensively in the literature for example as used in self-tanning dihydroxyacetone formulations having improved stability and providing enhanced delivery The prior art does not disclose additives specifically added to sunless tanning compositions to reduce water activity.

In order to identify cosmetic or pharmaceutical additives with the ability to significantly reduce water activity for possible use in sunless tanning formulations, various additives were screened using the Aqualab 3TE instrument. An arbitrary upper limit of 0.900 for aqueous solutions of additives was set for the screening studies. In other words, any cosmetic or pharmaceutical additive investigated must lower the $a_w$ of water from 1.000 to 0.900 or below when tested at a concentration that was judged to be the upper practical limit for inclusion based on safety and general cosmetic acceptability. Diglycols, polyols, and water soluble polymers screened did not meet the screening criteria, even when tested at up to 50% w/w concentrations.

However, two salts, sodium lactate and sodium pyrrolidone carboxylic acid (Sodium PCA) were capable of reducing the water activity to a greater extent than any other material screened and to a significantly lower level of water activity on a molar concentration basis when compared to polyols and diglycols.

Table 2 lists concentration of sodium lactate vs. corresponding $a_w$ values.

TABLE 2

| Sodium Lactate % w/w | Water Activity ($a_w$) |
| --- | --- |
| 6.0 | 0.991 |
| 12.0 | 0.944 |
| 18.0 | 0.913 |
| 24.0 | 0.880 |
| 30.0 | 0.840 |

At a concentration of between 18-24%, sodium lactate would meet the screening criterion of reduction of $a_w$ to 0.900 or less. Although use of sodium lactate at concentrations of 18-24% in sunless tanning formulations would be safe and could be made aesthetically acceptable, evaluation of this material began at lower concentrations with the understanding that the in vivo water activity of the sodium lactate formulation would be greater than the ex vivo water activity due to surface evaporation after application to the skin and therefore a higher relative concentration of sodium lactate would penetrate and concentrate in the top layers of the stratum corneum upon application.

Simple aqueous formulations of dihydroxyacetone and sodium lactate were first evaluated for tanning response on skin. The formulations evaluated and the tanning responses obtained are shown in Tables 3 (formulations) and Table 4 (tanning response of Table 3 formulas).

TABLE 3

| | Formulas 26-115 (% w/w) | | |
| --- | --- | --- | --- |
| Ingredients | A | B | C |
| DHA | 10.0 | 10.0 | 10.0 |
| Sodium Lactate | 3.0 | 6.0 | 12.0 |
| Deionized Water | 87.0 | 84.0 | 78.0 |

TABLE 4

| Formula | Tanning Response (24 hrs.) |
| --- | --- |
| A | 4.5 |
| B | 2.5 |
| C | 2.0 |
| Control | 6.0 |

An equal amount of each formula (approximately 150 mg.) from Table 3 was applied to 2"×2" adjacent sections of forearm, allowed to dry and covered with clothing for the duration of the testing. The application areas were visibly the same color prior to treatment with the solutions and this was confirmed via calorimeter readings. Visual assessment of color development was made 24 hours post application using a 1-6 point scale with 1 signifying no color development versus non-treated skin, 3 signifying moderate color development and 6 signifying intensely dark color development. Color development scores are shown in table 4. A commercial sunless tanning solution containing 10% DHA was used as a positive control.

Surprisingly, the lowest level of sodium lactate (3%) gave the best tanning response of the experimental formulas containing lactate salt.

Further studies were conducted to explore the effect of even lower levels of sodium lactate with DHA with and without pH adjustment. It is well known that the stability of DHA is affected by pH and that shelf stable solutions of DHA should be in the range of pH 3.0-6.0 and preferably between pH 3.0-4.5. The formulas evaluated are shown in Table 5 below.

TABLE 5

| | Formulas 26-121-(% w/w) | | | | | |
| --- | --- | --- | --- | --- | --- | --- |
| Ingredient | A | B | C | D | E | F |
| Sodium Lactate | 1.0 | 3.0 | 5.0 | 1.0 | 3.0 | 5.0 |
| DHA | 10 | 10 | 10 | 10 | 10 | 10 |
| Butylene Glycol | 5 | 5 | 5 | 5 | 5 | 5 |
| Deionized Water | 84 | 82 | 80 | 84 | 82 | 80 |
| Citric Acid, 25% sol'n | * | * | * | ** | ** | ** |

\* pH adjusted to 5.0
\*\* pH adjusted to 3.5-4.5

As before, an equal amount of each formula (approximately 150 mg.) from Table 5 was applied to 2"×2" adjacent sections of forearm, allowed to dry and covered with clothing for the duration of the testing. The application areas were visibly the same color prior to treatment with the solutions and this was confirmed via colorimeter readings. Visual assessment of color development was made 24 hours and at 48 hours post application using a 1-6 point scale with 1 signifying no color development versus non-treated skin, 3 signifying moderate color development and 6 signifying intensely dark color development. Color development scores are shown in table 6.

TABLE 6

| Formula | Tanning response 24 hrs | Tanning response 48 hrs |
| --- | --- | --- |
| A | 5.0 | 4.0 |
| B | 4.5 | 3.0 |
| C | 5.0 | 3.5 |
| D | 5.5 | 4.0 |
| E | 4.5 | 3.0 |
| F | 3.5 | 2.0 |
| Control | 5.0 | 3.5 |

A control formula containing 10% DHA, 5% butylene glycol and 5% methylsulfonylmethane was used as a positive control. Past studies as outlined in applicants' co-pending application Ser. No. 10/382,868 titled SUNLESS TANNING PRODUCTS AND PROCESSES, filed on Mar. 5, 2003 have demonstrated the ability of methylsulfonylmethane (MSM) to enhance the tanning response of DHA.

The above study showed a similar tanning response of formulas with 1-5% sodium lactate and quite similar to the MSM positive control except for 5.0% concentration at pH 5.0 which had a lower tanning response.

Similar results to the above were obtained when sodium lactate, lactic acid, and sodium hydroxide were combined to give a total concentration of lactate within the above range of 1.0-5.0% sodium lactate in a pH range of 3.0-5.0 Further experiments were conducted with lactic acid or sodium lactate with pH adjusted to 3.0-4.0 with citric acid. The formulas are shown below in Table 7

TABLE 7

| Ingredients | Formulas 26-131 | |
| --- | --- | --- |
| | A | B |
| DHA | 10 | 10 |
| Sodium Lactate | 1.0 | — |
| Lactic Acid | — | 1.0 |
| Butylene Gylcol | 5 | 5 |
| Deionized Water | 84 | 84 |
| Citric Acid/NaOH | * | * |

The pH of formula A was adjusted to a pH of 3.45 with a 25% solution of citric acid and the pH of formula B was adjusted to a pH of 3.3 with a 25% solution of sodium hydroxide (NaOH). Similar tanning responses equal to a positive control containing MSM as described for Table 6 were recorded for the above two formulas. Additional experiments were conducted with sodium lactate or lactic acid added to 5% DHA solutions. Again, enhancement of the tanning response was recorded at the lower levels of DHA. The enhancement of tanning is essentially the same from sodium lactate added as a salt or made in situ via the addition of lactic acid and sodium hydroxide. Lactic acid has been cited as an example of an acidifying agent in the prior art employing self-tanning dihydroxyacetone formulations having improved stability and providing enhanced delivery. However, use of lactic acid for this purpose would typically be less than 0.5% and in the range of 0.01-0.5%.

In fact, the prior art specifically cites the concentration of acidifying agent of precise amounts depends upon both the strength and the concentration of the acidifying agent utilized, but will generally be in an amount of from about 0.01% to about 0.50% by weight, based on the total weight of said composition, preferably from about 0.02% to about 0.40% by weight, more preferably from about 0.03% to about 0.30% by weight, and most preferably from about 0.04% to about 0.20% by weight, based on the total weight of said composition.

Several other sunless tanning patents mention the possible use of lactic acid as an acidifying agent but no use concentrations are cited.

The skin moisturizing properties of sodium lactate are well known. A citation by Purac, Inc., a supplier of lactic acid and sodium lactate describes the humectant properties of PURASAL S©, Purac's Brand of sodium lactate as follows:

"Both lactic acid and lactates are very effective humectants. The main function of humectants is to keep the cosmetic product from drying out. The moisture loss figure shows that PURAC (lactic acid) and glycerin have an equal water-holding capacity, while PURASAL S (sodium lactate) has double the capacity of glycerin". (Source: A buffering humectant for cosmetics, Drug and cosmetic industry, by L. I. Osipow].

Various prior art references identify compositions and methods for imparting an artificial tan to human skin and imparting artificial tans and protecting the skin from ultraviolet radiation using ammonium and quarternary ammonium lactate salts as humectants in oil-in-water emulsions containing dihydroxyacetone as the tanning agent. The sunless tanning compositions cited contain non-water soluble ingredients, No enhancement of the tanning response is described for the ammonium or quarternary ammonium lactate salts.

In addition to the water activity screening and the tanning experiments conducted with simple aqueous solutions of DHA, sodium lactate, and glycols, objective instrumental testing for in vivo water binding capacity of these DHA-sodium lactate-glycol solutions was conducted.

In vivo experiments conducted with a Nova Dermal Phase Meter (NOVA is a trademark of the NOVA Technology Corp., Gloucester, Mass., USA.) dearly show that the addition of sodium lactate to aqueous solutions of DHA improve the water holding capacity of the stratum corneum and thus exert a moisturizing effect. The Nova Meter measures water content of the top layers of the skin indirectly via conductance measurements.

Lastly, follow-up studies conducted with aged and accelerated aged sunless tanning formulations containing sodium lactate show the formulations to be shelf stable.

The various experiments conducted show that aqueous solutions of sodium lactate:
  Significantly reduce water activity ($A_w$) below 0.900 at concentrations of 25% w/w or less
  Enhance the tanning response of DHA at use concentrations of 0.5-5.0%
  Have sustained in vivo dermal water binding properties at use concentrations
  Produce shelf stable formulations with DHA and are compatible and non-reactive with DHA formulations in the acid range (pH 3.0-6.0)

Although not listed in the simple aqueous solutions that combine DHA, glycols or diglycols, sodium lactate or lactic acid, and acidifying or alkalizing agents used in the above formulations to illustrate the use of sodium lactate or lactic acid to enhance automated sunless tanning spray formulations, these formulations may also contain water soluble antimicrobial agents, antioxidants, botanicals, buffering agents, chelating agents, coloring additives, cosmeceuticals, defoaming agents, dermatological agents, dispersing agents, emollients, other humectants or moisturizers, fragrances, preservatives, polyols or sugars, sunscreen agents, surfactants, and vitamins.

While the examples set forth above illustrate specific embodiments of the invention and should be considered non-limiting examples with variations and modifications thereof all being within the scope and sphere of this invention.

What is claimed is:

1. A sprayable, aqueous, sunless tanning composition consisting of:
  a) dihydroxyacetone at a concentration of from 0.5% to 20% by weight of the composition;
  b) at least one humectant salt at a concentration of from 0.5% to 5% by weight of the composition, said humectant salt selected from the group consisting of sodium lactate and sodium pyrrolidone carboxylic acid, wherein an aqueous solution of said humectant salt exhibits a water activity of 0.90 or less when the humectant salt is present in the aqueous solution at a concentration of from about 18% to about 24% by weight of the solution;

c) at least one diol selected from 1,2-pentanediol and isoprene glycol; and
d) an aqueous carrier vehicle.

2. A sprayable, aqueous, sunless tanning composition according to claim 1 having a pH in the range of 3.0-6.0.

3. A sprayable, aqueous, sunless tanning composition according to claim 2 wherein the diol is 1,2-pentane diol.

4. A sprayable, aqueous sunless tanning composition according to claim 2 having a pH in the range of 3.0-4.5.

5. The sprayable aqueous sunless tanning composition of claim 1 wherein the humectant salt is sodium lactate.

* * * * *